(12) United States Patent
Freyman et al.

(10) Patent No.: US 7,686,788 B2
(45) Date of Patent: Mar. 30, 2010

(54) CATHETER HAVING A DISTAL DRUG DELIVERY UNIT AND METHOD OF USING SAME

(75) Inventors: Toby Freyman, Waltham, MA (US); Maria Palasis, Wellesley, MA (US); Wendy Naimark, Cambridge, MA (US); Timothy J. Mickley, Elk River, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 336 days.

(21) Appl. No.: 11/070,190

(22) Filed: Mar. 3, 2005

(65) Prior Publication Data

US 2006/0200083 A1 Sep. 7, 2006

(51) Int. Cl.
*A61M 5/00* (2006.01)
(52) U.S. Cl. ............... 604/181; 604/96.01; 604/97.02; 604/99.01; 604/124; 604/140; 604/142; 604/143; 604/146; 604/147; 604/151; 604/153; 604/185; 604/187; 604/212; 604/216; 604/217; 604/132; 604/133; 604/410
(58) Field of Classification Search ............... 604/96.01, 604/97.02, 99.01, 99.02, 118, 121, 124–125, 604/140–143, 146–147, 151, 153, 164.01, 604/181, 185, 187, 212, 216, 217, 90, 93.01, 604/95.02, 131, 132, 133, 150, 57–60, 64, 604/145, 410, 406
See application file for complete search history.

(56) References Cited

U.S. PATENT DOCUMENTS

| | | | | |
|---|---|---|---|---|
| 921,130 | A | * 5/1909 | Lockwood | .................. 604/141 |
| 3,965,897 | A | * 6/1976 | Lundquist | .................. 604/246 |
| 4,034,756 | A | * 7/1977 | Higuchi et al. | ........... 604/892.1 |
| 4,089,335 | A | * 5/1978 | Harris | ........................ 604/222 |
| 4,236,516 | A | * 12/1980 | Nilson | ........................ 604/214 |
| 4,578,061 | A | 3/1986 | Lemelson | |
| 4,790,819 | A | 12/1988 | Li et al. | |
| 4,902,278 | A | * 2/1990 | Maget et al. | ................. 604/132 |
| 5,135,498 | A | * 8/1992 | Kam et al. | ................... 604/140 |
| 5,306,246 | A | 4/1994 | Sahatijian et al. | |
| 5,318,540 | A | 6/1994 | Athayde et al. | |
| 5,358,493 | A | 10/1994 | Schweich, Jr. et al. | |
| 5,391,183 | A | 2/1995 | Janzen et al. | |
| 5,437,631 | A | 8/1995 | Janzen | |
| 5,443,181 | A | * 8/1995 | Popp et al. | ..................... 222/95 |
| 5,492,534 | A | * 2/1996 | Athayde et al. | ............. 604/141 |

(Continued)

FOREIGN PATENT DOCUMENTS

EP 0 202 658 A1 4/1989

(Continued)

*Primary Examiner*—Nicholas D Lucchesi
*Assistant Examiner*—Quynh-Nhu H Vu
(74) *Attorney, Agent, or Firm*—Kenyon & Kenyon LLP (57) ABSTRACT

A catheter having a drug delivery unit at the distal end thereof. The drug delivery unit includes an actuator capable of assuming an activated and an inactivated configuration. The drug delivery unit also includes a receptacle capable of accepting a therapeutic agent. The actuator and receptacle are in communication with each other such that the actuator transmits force to the receptacle and the receptacle accepts force from the actuator in an activated configuration of the actuator. Also provided is a method of delivering a therapeutic agent to a target site using the catheter of the present invention.

29 Claims, 8 Drawing Sheets

U.S. PATENT DOCUMENTS

| | | | |
|---|---|---|---|
| 5,545,133 A | 8/1996 | Burns et al. | |
| 5,553,741 A * | 9/1996 | Sancoff et al. | 222/1 |
| 5,558,642 A | 9/1996 | Schweich, Jr. et al. | |
| 5,649,959 A | 7/1997 | Hannam et al. | |
| 5,672,167 A * | 9/1997 | Athayde et al. | 604/892.1 |
| 5,700,245 A * | 12/1997 | Sancoff et al. | 604/145 |
| 5,702,384 A | 12/1997 | Umeyama et al. | |
| 5,707,361 A * | 1/1998 | Slettenmark | 604/131 |
| 5,738,657 A * | 4/1998 | Bryant et al. | 604/145 |
| 5,746,728 A | 5/1998 | Py | |
| 5,766,157 A | 6/1998 | Tilton, Jr. | |
| 5,772,629 A | 6/1998 | Kaplan | |
| 5,807,311 A | 9/1998 | Palestrant | |
| 5,820,610 A | 10/1998 | Baudino | |
| 5,833,658 A | 11/1998 | Levy et al. | |
| 5,840,061 A | 11/1998 | Menne et al. | |
| 5,845,646 A | 12/1998 | Lemelson | |
| 5,897,097 A * | 4/1999 | Biegelsen et al. | 251/129.01 |
| 6,004,295 A | 12/1999 | Langer et al. | |
| 6,050,986 A | 4/2000 | Hektner | |
| 6,398,760 B1 * | 6/2002 | Danby | 604/132 |
| 2003/0069547 A1 | 4/2003 | Gonon | |
| 2005/0038406 A1 * | 2/2005 | Epstein et al. | 604/500 |
| 2005/0149097 A1 | 7/2005 | Regnell et al. | |

FOREIGN PATENT DOCUMENTS

| | | |
|---|---|---|
| EP | 0 202 658 B1 | 4/1989 |
| WO | WO 98/10824 | 3/1998 |

* cited by examiner

FIG. 16 though the catheter to reach the target site. In general, referring to FIG. 1, the
CATHETER HAVING A DISTAL DRUG DELIVERY UNIT AND METHOD OF USING SAME

FIELD OF THE INVENTION

The present invention relates to a catheter having a drug delivery unit at the distal end thereof for delivering a therapeutic agent to a target site of the body.

BACKGROUND OF THE INVENTION

A catheter is a hollow flexible tube that is often fitted at its distal end with a hypodermic needle or a drug delivery balloon to deliver a therapeutic agent to a target site in the body. For such an application, the proximal end of the catheter will accept or be manufactured with a syringe that is capable of holding a therapeutic agent. To deliver the therapeutic agent using such a catheter, the syringe is filled with the therapeutic agent, pressure is applied to the syringe to force the therapeutic agent into the catheter, and the therapeutic agent is ejected from the catheter's distal end to the target site.

Such a method of drug delivery presents several disadvantages. For instance, such a method is highly inefficient as the entire catheter lumen must be filled with the therapeutic agent before even a small amount can be ejected from the catheter into the target site. In addition, because the therapeutic agent is loaded into the catheter through the proximal end and must pass through the entire length of the catheter to reach the target site, an amount of therapeutic agent inevitably remains in the catheter lumen after delivery. This amount is simply disposed of after delivery, which adds to the expense of the drug delivery procedure. Moreover, it is difficult for viscous, semi-solid or gel-like materials to pass through the entire length of these existing catheters. Accordingly, there is a need for an efficient catheter that reduces the amount of undelivered therapeutic agent and that improves the delivery of a viscous therapeutic agent to the target site.

SUMMARY OF THE INVENTION

The present invention provides a catheter having an infusion lumen extending partially therethrough and having a drug delivery unit at the distal end of the catheter. The drug delivery unit comprises an actuator and a receptacle. The actuator is capable of assuming an activated configuration and an inactivated configuration and is in fluid communication with the infusion lumen of the catheter. The receptacle is in communication with the actuator such that the actuator transmits force to the receptacle and the receptacle accepts force from the actuator in an activated configuration of the actuator.

The present invention also provides a catheter comprising an inner shaft and an outer shaft disposed around the inner shaft. The inner shaft has an infusion lumen extending partially therethrough and has a distal end comprising a drug delivery unit. The drug delivery unit comprises an actuator and a receptacle. The actuator is capable of assuming an activated configuration and an inactivated configuration and is in fluid communication with the infusion lumen. The receptacle is in communication with the actuator such that the actuator transmits force to the receptacle and the receptacle accepts force from the actuator in an activated configuration of the actuator.

The present invention also provides a method of delivering a therapeutic agent to a target site comprising providing a catheter having a distal end comprising a drug delivery unit, placing the therapeutic agent in the drug delivery unit, and delivering the therapeutic agent to the target site.

BRIEF DESCRIPTION OF THE INVENTION

The present invention will become more fully understood from the detailed description given hereinbelow and the accompanying drawings which are given by way of illustration only. It should be understood that the present invention is in no way limited to the particular arrangement or inclusion of components depicted in the accompanying drawings and wherein.

DETAILED DESCRIPTION OF THE INVENTION

Figure 1:
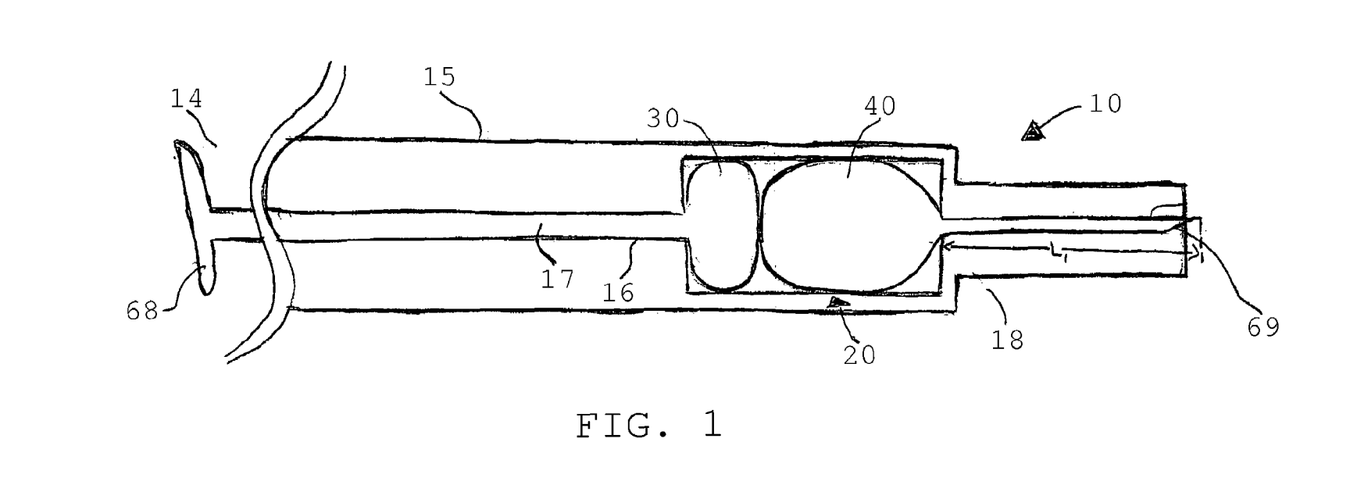
FIG. 1 is a side view of a catheter according to the present invention.
Figure 2:
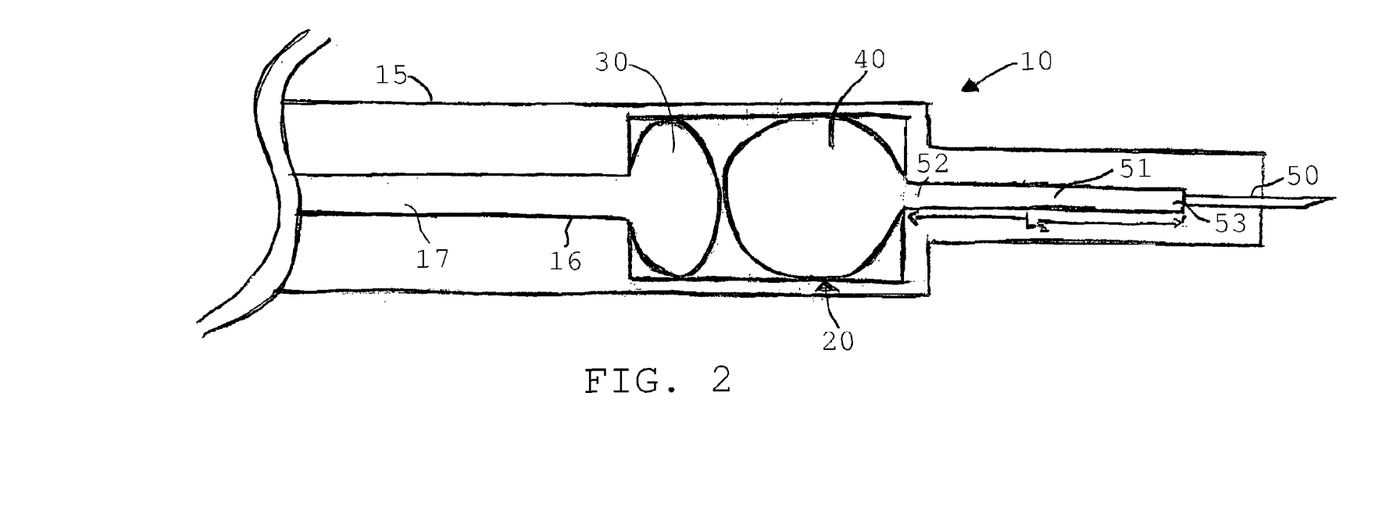
FIG. 2 is a side view of a catheter according to the present invention depicting an alternative embodiment of a drug delivery unit.

The present invention provides a catheter having a drug delivery unit at the distal end thereof to effectively shorten the distance a therapeutic agent must travel through the catheter to reach the target site. In general, referring to FIG. 1, the present invention provides a catheter 10 having an infusion lumen 17 extending partially therethrough and a drug delivery unit 20 located at the distal end 18 of catheter 10. Drug delivery unit 20 comprises an actuator 30 in fluid communication with infusion lumen 17 and a receptacle 40 in communication with actuator 30. Actuator 30 is capable of having an inactivated configuration and an activated configuration and receptacle 40 is capable of receiving a therapeutic agent. Actuator 30 and receptacle 40, according to the present invention, are in communication with each other such that actuator 30 transmits force to receptacle 40 and receptacle 40 accepts force from actuator 30 in an activated configuration of actuator 30. Receptacle 40 may be in communication with any structure that is capable of transmitting a therapeutic agent to a target site. For example, as illustrated in FIG. 1, receptacle 40 may be in fluid communication with a needle 50. Alternatively, receptacle 40 may be in fluid communication in a drug delivery balloon (not shown). Referring to FIG. 2, drug delivery unit 20 may also have a drug delivery lumen 51 extending partially therethrough that has one end 52 in fluid communication with receptacle 40 and that has another end 53 in fluid communication with needle 50 (or in communication with a drug delivery balloon). As illustrated in FIGS. 1 and 2, catheter 10 may comprise an outer shaft 15 disposed around an inner shaft 16 and inner shaft 16 has the infusion lumen 17 extending partially therethrough and has the drug delivery unit 20 at the distal end 18.

In general, to deliver a therapeutic agent to a target site using catheter 10 of the present invention, a therapeutic agent is placed in receptacle 40 of drug delivery unit 20 and an infusion material is loaded in catheter 10 through proximal end 14 of catheter 10, which may comprise a handle 68. Such infusion material travels down infusion lumen 17 to actuator 30 causing actuator 30 to move from an inactivated configuration, wherein no force or nominal force is transmitted to receptacle 40, to an activated configuration, wherein force is transmitted to receptacle 40. When force is transmitted to receptacle 40, the therapeutic agent is forced out of receptacle 40 through needle 50 to the target site or through drug delivery lumen 51 and then through needle 50 to the target site.

With respect to more specific details of the present invention, actuator 30 and receptacle 40 of drug delivery unit 20 can be any structures that can serve the respective functions of actuator 30 and receptacle 40. In particular, actuator 30 can be any structural component that can transmit force to receptacle 40 and receptacle 40 can be any structural component that can accept force from actuator 30 and that can store a therapeutic agent. For example, actuator 30 may be a balloon, piston, plunger, spring-loaded coil, or a self-expanding stent-like structure and receptacle 40 may be a balloon or a size-adjustable chamber.

Figure 3:
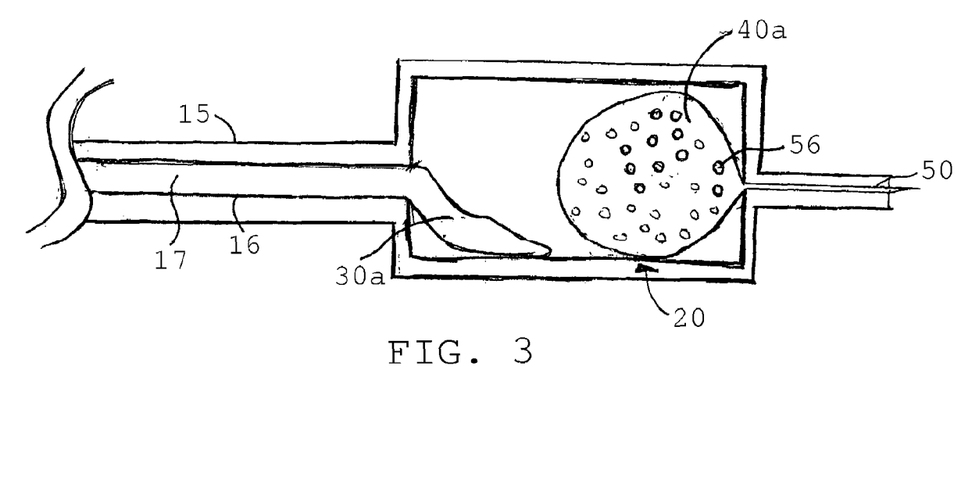
FIG. 3 is a side view of a catheter according to the present invention depicting an embodiment of a drug delivery unit with an actuator in an inactivated configuration.
Figure 4:
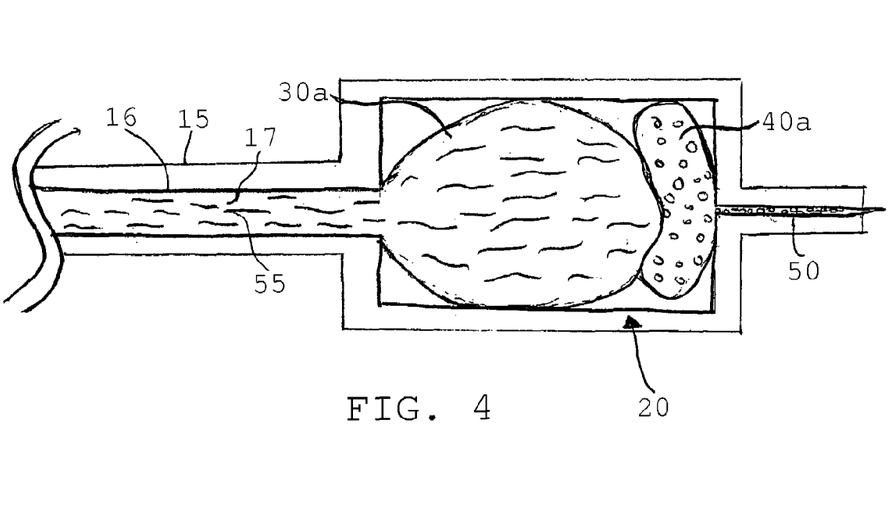
FIG. 4 is similar to FIG. 3 but with the actuator in an activated configuration.

Referring to FIGS. 3-4, in one embodiment of the present invention, the actuator and receptacle are both balloons, 30a and 40a, respectively. In such an embodiment, in an inactivated configuration, balloon 30a is in a collapsed or deflated state as shown in FIG. 3 and does not transmit force to balloon 40a, which is shown containing a therapeutic agent 56. Referring to FIG. 4, balloon 30a assumes an activated configuration when an infusion material 55 passes through infusion lumen 17 to access and inflate balloon 30a. Such infusion material 55 can be any material that can inflate balloon 30a to bring balloon 30a to an activated configuration. For example, infusion material 55 can be water, saline, air or any other gaseous, liquid, or semi-solid substance. Once in an activated configuration, balloon 30a transmits force to balloon 40a thereby urging therapeutic agent 56 out from balloon 40a as shown in FIG. 4.

Figure 5:
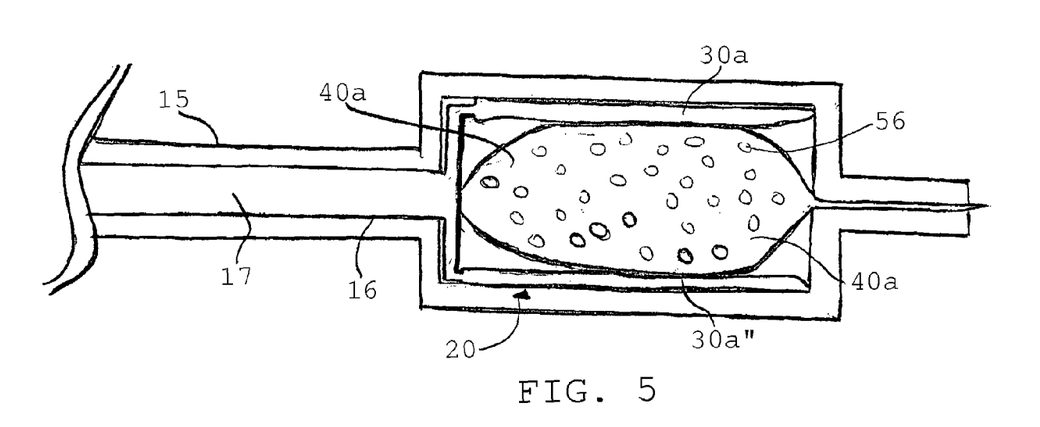
FIG. 5 is a side view of a catheter according to the present invention depicting an alternative embodiment of a drug delivery unit with an actuator in an inactivated configuration.
Figure 6:
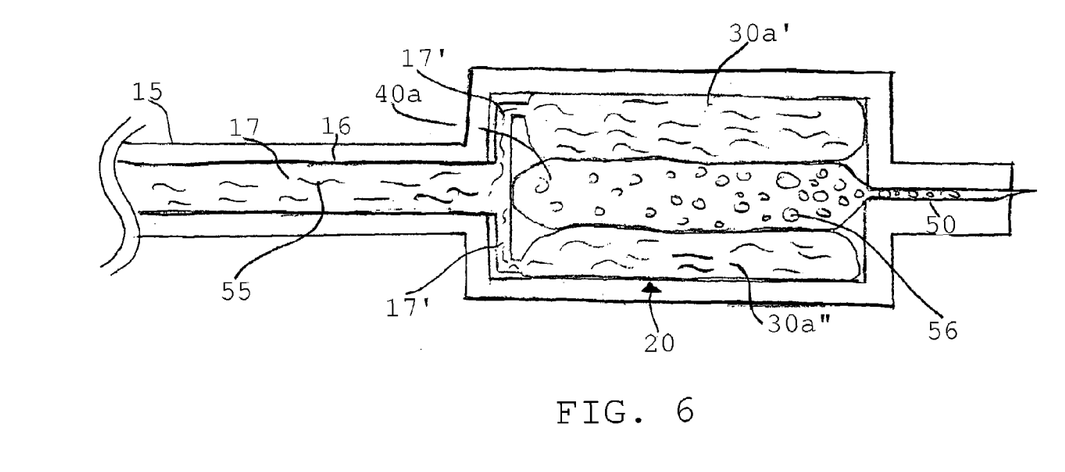
FIG. 6 is similar to FIG. 5 but with the actuator in an activated configuration.

Although in FIGS. 1-4, the actuator and receptacle are shown as both being single balloons with the receptacle located distal of the actuator, the present invention contemplates other arrangements of the actuator and the receptacle within drug delivery unit 20. For example, referring to FIGS. 5-6, in another embodiment, the actuator comprises balloons, 30a' and 30a'', and the receptacle comprises balloon 40a located between balloons 30a' and 30a''. In this embodiment, in an inactivated configuration, balloons 30a' and 30a'' are both in a collapsed or deflated state as shown in FIG. 5 and transmit no force or nominal force to balloon 40a, which is shown containing a therapeutic agent 56. Referring to FIG. 6, balloons 30a' and 30a'' assume an activated configuration when an infusion material 55, passes through infusion lumen 17 to access and inflate balloons 30a' and 30a''. In particular, in this embodiment, infusion lumen 17 bifurcates into two separate lumens 17' and 17'' with lumen 17' in fluid communication with balloon 30a' and lumen 17'' in fluid communication with balloon 30a''. Accordingly, to activate balloon 30a', infusion material 55 passes through infusion lumen 17 and then infusion lumen 17' to access and inflate balloon 30a'. To activate balloon 30a'', infusion material 55 passes through infusion lumen 17 and then infusion lumen 17'' to access and inflate balloon 30a''. Once in an activated configuration, both balloons 30a' and 30a'' mutually transmit force to balloon 40a thereby urging therapeutic agent 56 out from balloon 40a as shown in FIG. 6.

Figure 7:
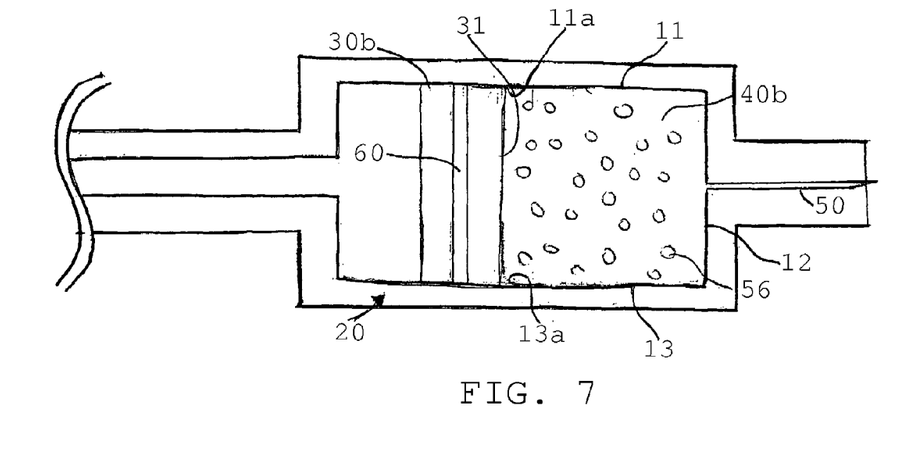
FIG. 7 is a side view of a catheter according to the present invention depicting an alternative embodiment of a drug delivery unit with an actuator in an inactivated configuration.
Figure 8:
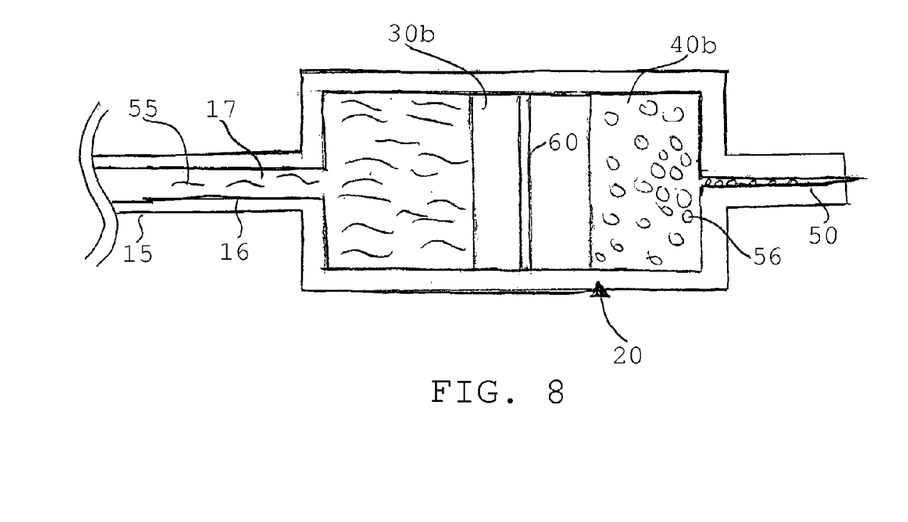
FIG. 8 is similar to FIG. 7 but with the actuator in an activated configuration.

Referring to FIGS. 7-8, in another embodiment of the present invention, the actuator is a slidable piston 30b having a force application surface 31 and the receptacle is a size-adjustable chamber 40b. In particular, chamber 40b is defined by side surfaces 11, 12, and 13 of distal delivery unit 20 and force application surface 31 of piston 30b. In an inactivated configuration, piston 30b is in a stationary position, as shown in FIG. 7, and transmits no force or nominal force to chamber 40b, which is shown containing a therapeutic agent 56. Referring to FIG. 3 piston 30b assumes an activated configuration when infusion material 55 is injected into and passes through infusion lumen 17 to access and propel forward piston 30b. Once in an activated configuration, piston 30b transmits force to chamber 40b, which in this embodiment, effectively reduces the volume of chamber 40b urging therapeutic agent 56 out from chamber 40b. Preferably, piston 30b is situated in relation to catheter 10 to provide a substantially fluid tight seal such that no infusion material 55 commingles with therapeutic agent 56. For example, as shown in FIGS. 7-8, piston 30b may have an O-ring 60 disposed therearound that contacts opposing inner side surfaces 11a and 13a of catheter 10. Alternatively, piston 30b may be slidably received within catheter 10 by a close tolerance fit between the outer surface of piston 30b and opposing inner side surfaces 11a and 13a of catheter 10. Other methods of providing a substantially fluid tight seal are known in the art, such as metal rings, plastic rings, and multiple O-rings, all having various shapes and configurations.

Figure 9:
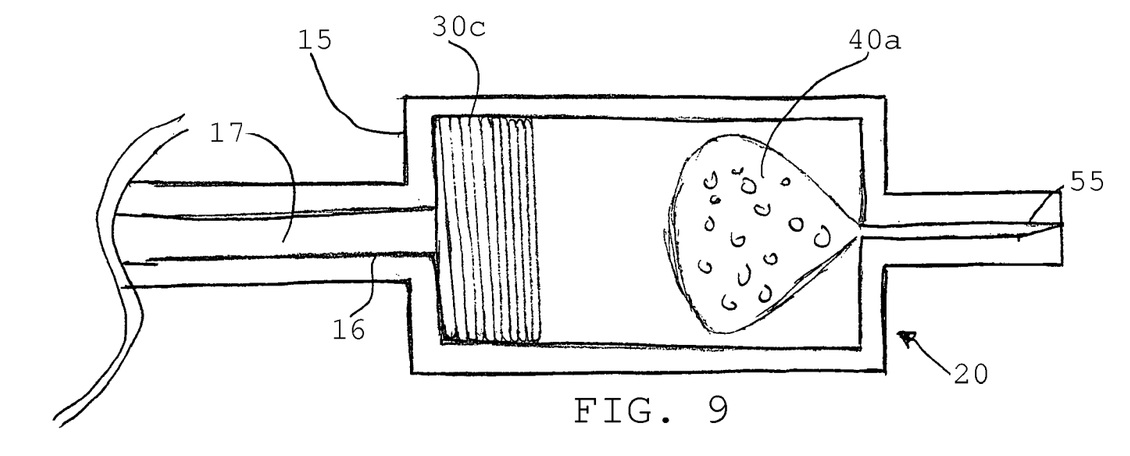
FIG. 9 is a side view of a catheter according to the present invention depicting an alternative embodiment of an actuator in an inactivated configuration.
Figure 10:
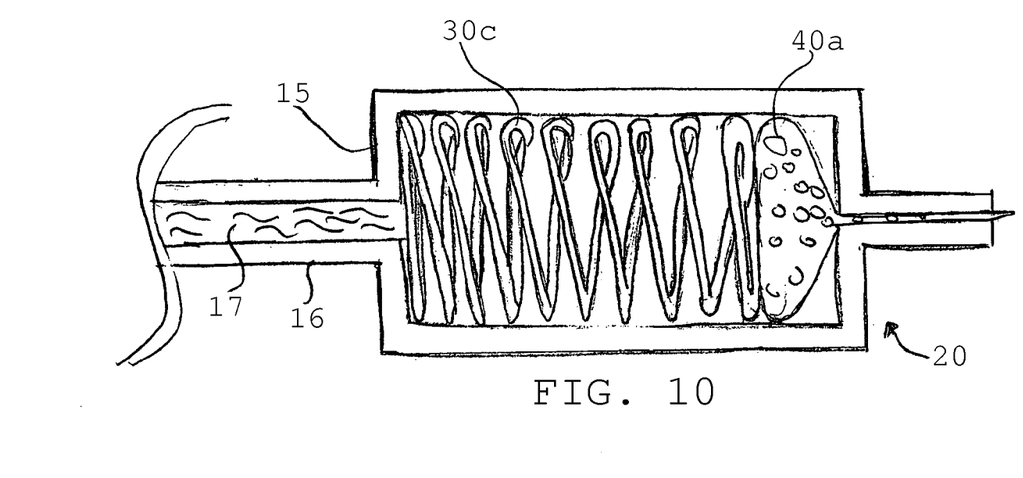
FIG. 10 is similar to FIG. 9 but with the actuator in an activated configuration.

Referring to FIGS. 9-10, in another embodiment of the present invention, the actuator is a spring-loaded coil 30c. Upon activation by an infusion material 55, coil 30c transitions from an inactivated configuration, in which it is wound as shown in FIG. 9, to an activated configuration, in which it extends closer to its equilibrium position as shown in FIG. 10 and transmits force to the receptacle, which is shown as a balloon 40a, thereby urging therapeutic agent 56 out from balloon 40a. Alternatively, coil 30c could be activated by a wire at the proximal end of catheter 10. For example, in an inactivated configuration of coil 30c, coil 30c is restrained by the wire, which is in a tensioned state. Upon release of the wire from the proximal end of the catheter, the coil advances forward in its activated configuration and transmits force to balloon 40a. Although this embodiment can be used to deliver any type of therapeutic agent, it is particularly suitable to transmit a viscous therapeutic agent since coil 30c is spring loaded and can therefore transmit sufficient force to the receptacle.

Figure 11:
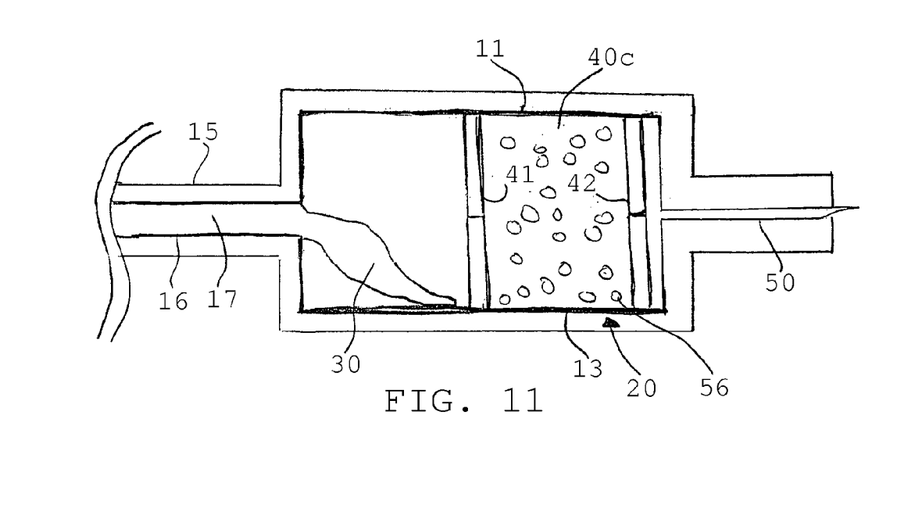
FIG. 11 is a side view of a catheter according to the present invention depicting an alternative embodiment of a receptacle with the actuator in an inactivated configuration.
Figure 12:
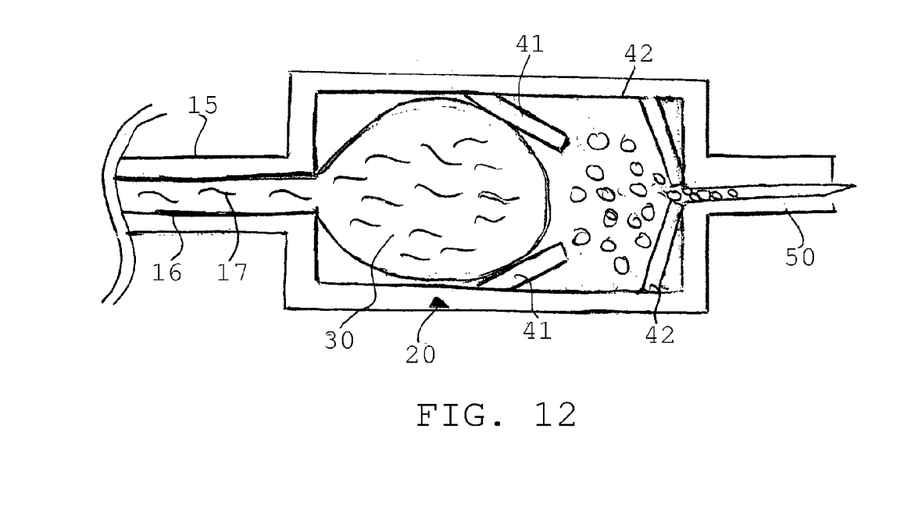
FIG. 12 is similar to FIG. 11 but with the actuator in an activated configuration.
Figure 13:
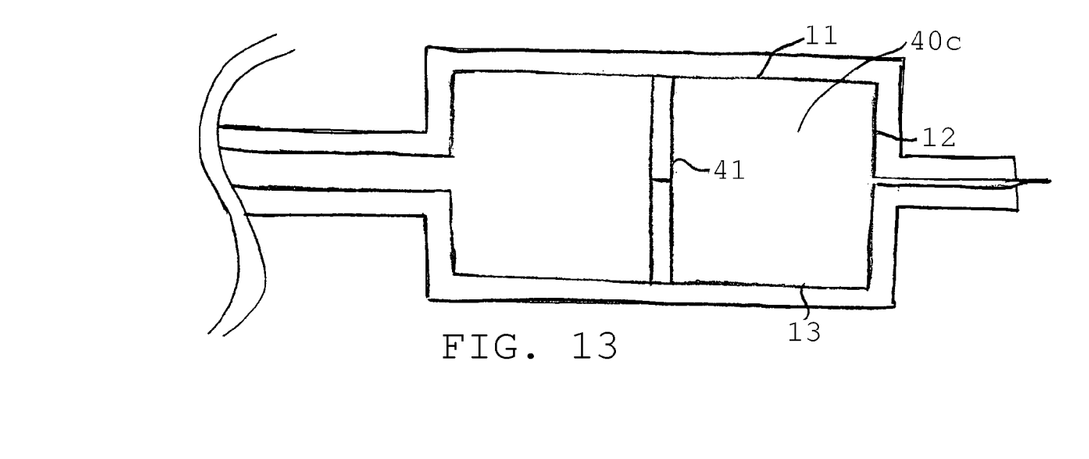
FIG. 13 is a side view of a catheter according to the present invention depicting an alternative embodiment of a receptacle.

Referring to FIGS. 11-12, in another embodiment of the present invention, the receptacle is a chamber 40c having a front end defined by a first pressure-sensitive gate 41 and a back end defined by a second pressure sensitive gate 42. Chamber 40c is further defined by side surfaces 11 and 13 of distal delivery unit 20. Therapeutic agent 56 is held between first and second gates 41 and 42 and both gates are capable of opening upon the application of pressure to the surfaces thereof. In this embodiment, in an inactivated configuration, the actuator 30 (which is shown as a balloon) transmits no force or nominal force to chamber 40c and therefore gates 41 and 42 are in a closed position as shown in FIG. 11. In an activated configuration, actuator 30 transmits force to first and second gates 41 and 42 causing the gates to open and release therapeutic agent 56 as shown in FIG. 12. Although, chamber 40c is shown in FIGS. 11-12 as being defined by two pressure sensitive gates 41 and 42, chamber 40c can also be defined by only first pressure-sensitive gate 41 and side surfaces 11-13 of distal delivery unit 20 as illustrated in FIG. 13. In the embodiment illustrated in FIG. 13, therapeutic agent 56 (not shown) is held between first gate 41 and side surface 12 and upon transmission of force by actuator 30 (not shown), gate 41 opens and therapeutic agent 56 is released from chamber 40c.

Figure 14:
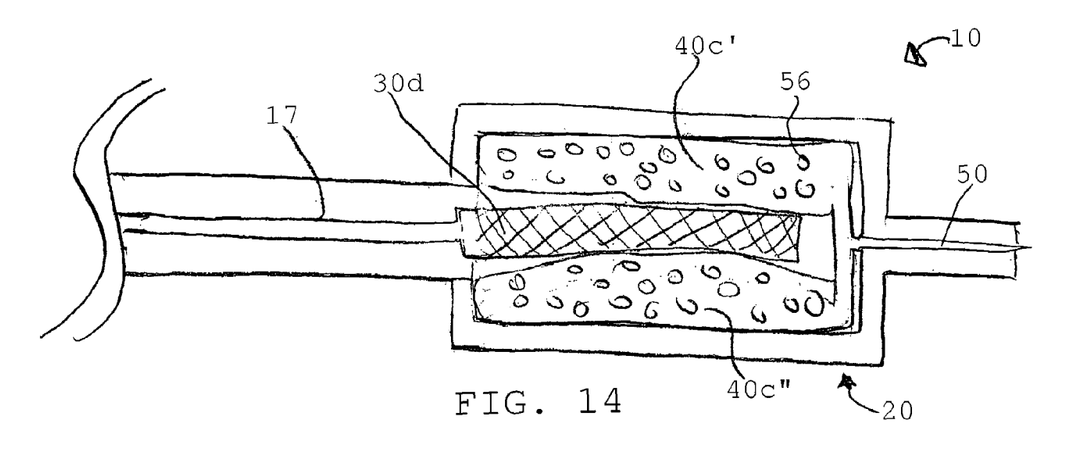
FIG. 14 is a side view of a catheter according to the present invention depicting an embodiment of a drug delivery unit with an actuator in an inactivated configuration.
Figure 15:
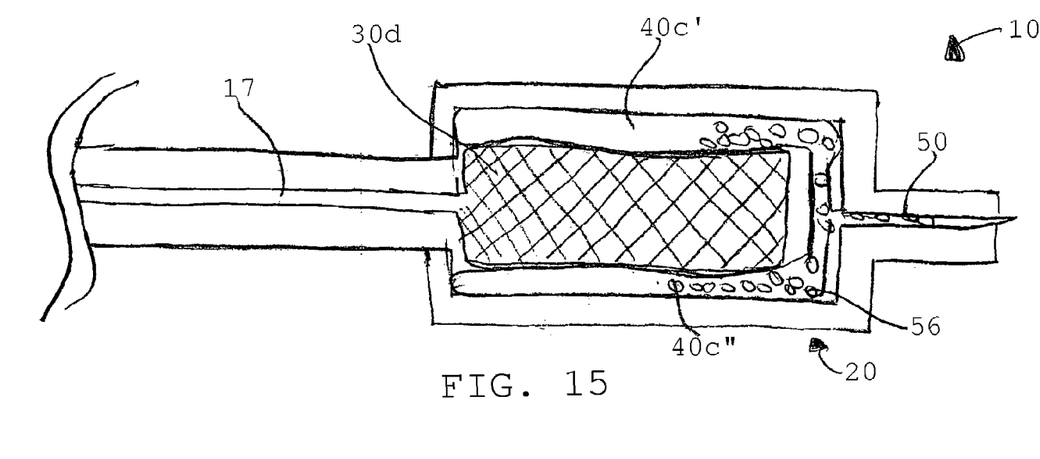
FIG. 15 is similar to FIG. 14 but with the actuator in an activated configuration.

Referring to FIGS. 14 and 15, in another embodiment of the present invention, the receptacle comprises balloons 40c' and 40c'' that are in communication with a needle 50 (although they may alternatively be in communication with a drug delivery balloon) and the actuator comprises a member 30d fabricated of a temperature-sensitive material such as, for example, a shape memory material, like nitinol or a self-expanding polymeric material. The actuator is also in communication with infusion lumen 17. Although in FIGS. 14 and 15, member 30d is depicted as having a stent-like shape, member 30d may have any other appropriate shape that allows it to make contact with balloons 40c' and 40c'' in an activated configuration. Member 30d is activated by a heated substance that passes through infusion lumen and contacts member 30d creating an exothermic chemical reaction within member 30d. Alternatively, an electrical resistive heating element could be used to generate an increase in When the transition temperature for member 30d is attained, member 30d expands, applies pressure to balloons 40c' and 40c'' and forces the therapeutic agent 56 within such balloons out of catheter 10. To provide multiple deliveries of therapeutic agents, individual members 30d could be arranged end to end in catheter 10 and activated individually.

It should be understood that the above embodiments of drug delivery unit 20 are in no way limited to particular combinations of actuator 30 and receptacle 40. In other words, any of the embodiments of actuator 30 described above or within the knowledge of one of skill in the art can be used in combination with any of the embodiments of receptacle 40 described above or within the knowledge of one of skill in the art. For example, drug delivery unit 20 can comprise an actuator 30 that is a balloon 30a and receptacle 40 that is a chamber 40b, or an actuator 30 that is a piston 30b and a receptacle 40 that is a balloon 40a, etc. Furthermore, multiple actuators 30 can be used in combination to transmit force to receptacle 40 if desired. For example, spring-loaded coil 30c could be used together with piston 30b to transmit force to receptacle 40. Specifically, an infusion material 55 could actuate coil 30c which would transmit force to piston 30b, which, in turn, would transmit force to receptacle 40 to release therapeutic agent 56 to the target site.

As mentioned previously, in any of the above-described embodiments, drug delivery unit 20 may include needle 50 in fluid communication with receptacle 40 as seen in FIG. 1. Alternatively, drug delivery unit 20 may further define a drug delivery lumen 51 extending partially therethrough which is in fluid communication with receptacle 40 at one end 52 and is in fluid communication with needle 50 at another end 53 as shown in FIG. 2. Whether drug delivery unit 20 comprises a needle 50 or defines a drug delivery lumen 51 which is in communication with needle 50 may depend, for example, on the intended use of the catheter. For example, the portion of drug delivery unit 20 defining drug delivery lumen 51 may be as flexible as the rest of catheter 10 and in such case if more flexibility is desired at distal end 18 of catheter 10, drug delivery unit 20 may define a drug delivery lumen 51 in communication with needle 50. Preferably length $L_1$ of needle 50, as indicated in FIG. 1 and length $L_2$ of drug delivery lumen 51, as indicated in FIG. 2, is about six inches.

Figure 16:
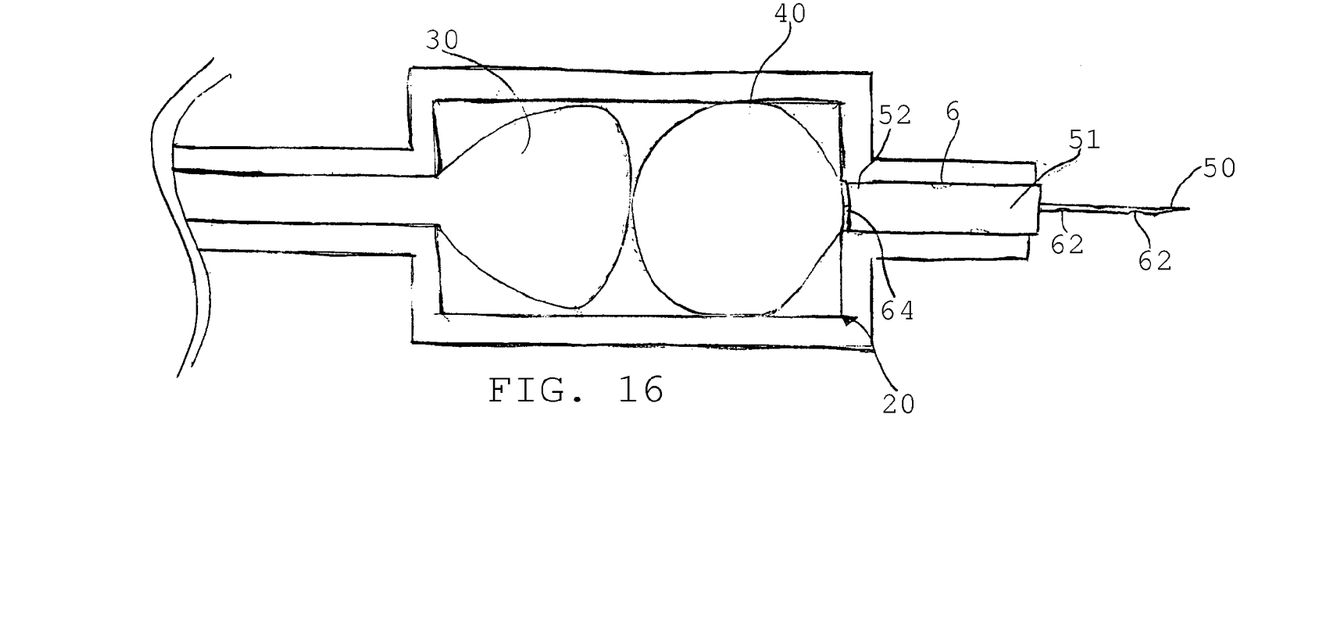
FIG. 16 is a side view of a catheter according to the present invention depicting an alternative embodiment of a drug delivery unit.

Referring to FIG. 16, to potentially prevent unwanted leakage of therapeutic agent 56 from receptacle 40 to drug delivery lumen 51 prior to delivery, drug delivery unit 20 may include a pressure-sensitive septum, valve, or membrane 64 at end 52 of drug delivery lumen 51. Membrane 64, according to the present invention, opens upon application of pressure to allow therapeutic agent 56 to pass from receptacle 40 to drug delivery lumen 51. Of course, it is understood that membrane 64 may be present in any of the embodiments contemplated by the present invention and not just the embodiment illustratively depicted in FIG. 16. Alternatively, a negative pressure may be used to prevent unwanted leakage of therapeutic agent 56 from receptacle 40.

In any of the above mentioned embodiments, catheter 10 may comprise multiple drug delivery units and multiple actuators and receptacles within these multiple drug units or within single drug delivery units to provide for multiple deliveries of the same or different therapeutic agents.

In an exemplary method of using catheter 10 of the present invention to deliver a therapeutic agent to a target site, wherein actuator 30 and receptacle 40 are both balloons, 30a and 40a, both balloons 30a and 40a are initially prepared for delivery. In particular, balloon 30a is initially deflated and filled with a small quantity of air. A syringe or other appropriate device containing infusion material 55 is connected to proximal end 14 of inner shaft 16 or handle 68 of shaft 16 and a vacuum is created by pulling back on the syringe. Following this initial preparatory step, balloon 30a remains in an inactivated configuration, i.e. in a deflated state. With respect to preparing receptacle 40, balloon 40a is initially deflated and a therapeutic agent 56 is introduced into balloon 40a by inserting a syringe or other appropriate device into distal opening 69 of needle 50 (such distal opening being depicted in FIG. 1) and urging the therapeutic agent 56 out from the syringe into balloon 40a. Catheter 10 is then ready for delivery and distal end 18 is positioned adjacent to the target site using any catheter guiding system known to one of skill in the art. Once contact with the target site is considered sufficient, inner shaft 16 is advanced through outer shaft 15 (handle 68 may be gripped by the user to advance inner shaft 16). Needle 50 exits the distal end of outer shaft 15 to penetrate and engage the target site. Next, pressure is applied to the syringe containing infusion material 55 connected to proximal end 14 of inner shaft 16 to introduce infusion material 55 into infusion lumen 17 of shaft 16. Infusion material 55 passes through infusion lumen 17 and enters and inflates balloon 30a bringing balloon 30a into an activated configuration. As balloon 30a inflates, it transmits force to balloon 40a sufficient to cause balloon 40a to deflate and release therapeutic agent 56 through needle 50 into the target site. Following delivery of therapeutic agent 56, needle 50 is retracted into outer shaft 15 and catheter 10 is removed or repositioned for additional delivery of therapeutic agent. Of course, the foregoing description of a method of using catheter 10 to deliver therapeutic agent 56 to a target site is merely exemplary and there are many other ways as will be readily appreciated by one of skill in the art to prepare catheter 10 for therapeutic agent delivery and to perform such therapeutic agent delivery.

Catheter 10 according to the present invention can be incorporated into any type of catheter assembly known to one of skill in the art, such as infusion catheter assemblies, direct injection catheter assemblies or more complex catheter assemblies to deliver a therapeutic agent, diagnostic agent or any other type of agent to a target site. The therapeutic agents, according to the present invention, can be in a gaseous, liquid, solid, or semi-solid state. Such therapeutic agents include pharmaceutically active compounds, nucleic acids with and without carrier vectors such as lipids, compacting agents (such as histones), viruses (such as adenovirus, adenoassociated virus, retrovirus, lentivirus and α-virus), polymers, hyaluronic acid, proteins, cells and the like, with or without targeting sequences. Specific examples of therapeutic agents used in conjunction with the present invention include, for example, pharmaceutically active compounds, proteins, cells, oligonucleotides, ribozymes, anti-sense oligonucleotides, DNA compacting agents, gene/vector systems (i.e., any vehicle that allows for the uptake and expression of nucleic acids), nucleic acids (including, for example, recombinant nucleic acids; naked DNA, cDNA, RNA; genomic DNA, cDNA or RNA in a non-infectious vector or in a viral vector and which further may have attached peptide targeting sequences; antisense nucleic acid (RNA or DNA); and DNA chimeras which include gene sequences and encoding for ferry proteins such as membrane translocating sequences ("MTS") and herpes simplex virus-1 ("VP22")), and viral, liposomes and cationic and anionic polymers and neutral polymers that are selected from a number of types depending on the desired application. Non-limiting examples of virus vectors or vectors derived from viral sources include adenoviral vectors, herpes simplex vectors, papilloma vectors, adeno-associated vectors, retroviral vectors, and the like. Non-limiting examples of biologically active solutes include anti-thrombogenic agents such as heparin, heparin derivatives, urokinase, and PPACK (dextrophenylalanine proline arginine chloromethylketone); anti-restenosis agents such as cladribine; antioxidants such as probucol and retinoic acid; angiogenic and anti-angiogenic agents and factors; anti-proliferative agents such as enoxaprin, angiopeptin, rapamycin, angiopeptin, monoclonal antibodies capable of blocking smooth muscle cell proliferation, hirudin, and acetylsalicylic acid; statins; angiotensin converting enzyme (ACE) inhibitors; beta-blockers; anti-inflammatory agents such as dexamethasone, prednisolone, corticosterone, budesonide, estrogen, sulfasalazine, acetyl salicylic acid, and mesalamine; calcium entry blockers such as verapamil, diltiazem and nifedipine; antineoplastic/antiproliferative/anti-mitotic agents such as paclitaxel, 5-fluorouracil, methotrexate, doxorubicin, daunorubicin, cyclosporine, cisplatin, vinblastine, vincristine, epothilones, endostatin, angiostatin and thymidine kinase inhibitors; antimicrobials such as triclosan, cephalosporins, aminoglycosides, and nitrofurantoin; anesthetic agents such as lidocaine, bupivacaine, and ropivacaine; nitric oxide (NO) donors such as linsidomine, molsidomine, L-arginine, NO-protein adducts, NO-carbohydrate adducts, polymeric or oligomeric NO adducts; anti-coagulants such as D-Phe-Pro-Arg chloromethyl ketone, an RGD peptide-containing compound, heparin, antithrombin compounds, platelet receptor antagonists, anti-thrombin antibodies, anti-platelet receptor antibodies, enoxaparin, hirudin, warfarin sodium, Dicumarol, aspirin, prostaglandin inhibitors, platelet inhibitors and tick antiplatelet factors; vascular cell growth promoters such as growth factors, growth factor receptor antagonists, transcriptional activators, and translational promoters; vascular cell growth inhibitors such as growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin; cholesterol-lowering agents; vasodilating agents; agents which interfere with endogenous vasoactive mechanisms; survival genes which protect against cell death, such as anti-apoptotic Bcl-2 family factors and Akt kinase; and combinations thereof. Cells can be of human origin (autologous or allogenic) or from an animal source (xenogeneic), genetically engineered if desired to deliver proteins of interest at the insertion site and any modifications to such cells are routinely made by one skilled in the art. Non-limiting examples of cells include side population (SP) cells, lineage negative (Lin⁻) cells including Lin⁻CD34⁻, Lin⁻CD34⁺, Lin⁻cKit⁺, mesenchymal stem cells including mesenchymal stem cells with 5-aza, cord blood cells, cardiac or other tissue derived stem cells, whole bone marrow, bone marrow mononuclear cells, endothelial progenitor cells, skeletal myoblasts or satellite cells, muscle derived cells, go cells, endothelial cells, adult cardiomyocytes, fibroblasts, smooth muscle cells, adult cardiac fibroblasts +5-aza, genetically modified cells, tissue engineered grafts, MyoD scar fibroblasts, pacing cells, embryonic stem cell clones, embryonic stem cells, fetal or neonatal cells, immunologically masked cells, and teratoma derived cells.

Polynucleotide sequences useful in practice of the invention include DNA or RNA sequences having a therapeutic effect after being taken up by a cell. Examples of therapeutic polynucleotides include anti-sense DNA and RNA; DNA coding for an anti-sense RNA; or DNA coding for tRNA or rRNA to replace defective or deficient endogenous molecules. The polynucleotides can also code for therapeutic proteins or polypeptides. A polypeptide is understood to be any translation product of a polynucleotide regardless of size, and whether glycosylated or not. Therapeutic proteins and polypeptides include as a primary example, those proteins or polypeptides that can compensate for defective or deficient species in an animal, or those that act through toxic effects to limit or remove harmful cells from the body. In addition, the polypeptides or proteins that can be injected, or whose DNA can be incorporated, include without limitation, angiogenic factors and other molecules competent to induce angiogenesis, including acidic and basic fibroblast growth factors, vascular endothelial growth factor, hif-1, epidermal growth factor, transforming growth factor alpha and beta, platelet-derived endothelial growth factor, platelet-derived growth factor, tumor necrosis factor alpha, hepatocyte growth factor and insulin like growth factor; growth factors; cell cycle inhibitors including CDK inhibitors; anti-restenosis agents, including p15, p16, p18, p19, p21, p27, p53, p57, Rb, nFkB and E2F decoys, thymidine kinase ("TK") and combinations thereof and other agents useful for interfering with cell proliferation, including agents for treating malignancies; and combinations thereof. Still other useful factors, which can be provided as polypeptides or as DNA encoding these polypeptides, include monocyte chemoattractant protein ("MCP-1"), and the family of bone morphogenic proteins ("BMPs"). The known proteins include BMP-2, BMP-3, BMP-4, BMP-5, BMP-6 (Vgr-1), BMP-7 (OP-1), BMP-8, BMP-9, BMP-10, BMP-11, BMP-12, BMP-13, BMP-14, BMP-15, and BMP-16. Currently preferred BMPs are any of BMP-2, BMP-3, BMP-4, BMP-5, BMP-6 and BMP-7. These dimeric proteins can be provided as homodimers, heterodimers, or combinations thereof, alone or together with other molecules. Alternatively or, in addition, molecules capable of inducing an upstream or downstream effect of a BMP can be provided. Such molecules include any of the "hedgehog" proteins, or the DNAs encoding them.

To provide controlled release of the therapeutic agents in embodiments where such a property is desired, the therapeutic agents may be microencapsulated with polymers to form a polymeric material/therapeutic agent matrix. Preferably, the polymer is characterized by all of the following: biocompatibility, controlled release characteristics, biodegradation capabilities, transfection capabilities, deterrence to the flocculation of the therapeutic agents, and sufficient density if utilized in aerosol form. Such a polymeric material/therapeutic agent matrix can be formed by admixing a therapeutic agent with a liquid polymer, in the absence of a solvent, to form a liquid polymer/therapeutic agent mixture. Curing of the mixture typically occurs in situ. To facilitate curing, a cross-linking or curing agent may be added to the mixture prior to application thereof. Addition of the cross-linking or curing agent to the polymer/therapeutic agent liquid mixture should not occur too far in advance of the application of the mixture in order to avoid over-curing of the mixture prior to application thereof. Curing may also occur in situ by exposing the polymer/therapeutic agent mixture, after application to the luminal surface, to radiation such as ultraviolet radiation or laser light, heat, or by contact with metabolic fluids such as water at the site where the mixture has been applied to the luminal surface. In coating systems employed in conjunction with the present invention, the polymeric material may be either bioabsorbable or biostable. Any of the polymers described herein that may be formulated as a liquid may be used to form the polymer/therapeutic agent mixture. When delivered into the target site, the therapeutic agent may be released from the polymer as it slowly dissolves into the aqueous bodily fluids and diffuses out of the polymer.

The polymer used in the present invention to encapsulate the therapeutic agent is preferably capable of absorbing a substantial amount of drug solution and may be hydrophilic or hydrophobic, and may be selected from the group consisting of polycarboxylic acids, cellulosic polymers, including cellulose acetate and cellulose nitrate, gelatin, polyvinylpyrrolidone, cross-linked polyvinylpyrrolidone, polyanhydrides including maleic anhydride polymers, polyamides, polyvinyl alcohols, copolymers of vinyl monomers such as EVA, polyvinyl ethers, polyvinyl aromatics, polyethylene oxides, glycosaminoglycans, polysaccharides, polyesters including polyethylene terephthalate, polyacrylamides, polyethers, polyether sulfone, polycarbonate, polyalkylenes including polypropylene, polyethylene and high molecular weight polyethylene, halogenated polyalkylenes including polytetrafluoroethylene, polyurethanes, polyorthoesters, proteins, polypeptides, silicones, siloxane polymers, polylactic acid, polyglycolic acid, polycaprolactone, polyhydroxybutyrate valerate and blends and copolymers thereof as well as other biodegradable, bioabsorbable and biostable polymers and copolymers. Encapsulation from polymer dispersions such as polyurethane dispersions (BAYHYDROL®, etc.) and acrylic latex dispersions are also within the scope of the present invention. The polymer may be a protein polymer, fibrin, collage and derivatives thereof, polysaccharides such as celluloses, starches, dextrans, alginates and derivatives of these polysaccharides, an extracellular matrix component, hyaluronic acid, or another biologic agent or a suitable mixture of any of these, for example. In one embodiment of the invention, the preferred polymer is polyacrylic acid, available as HYDROPLUS® (Boston Scientific Corporation, Natick, Mass.), and described in U.S. Pat. No. 5,091,205, the disclosure of which is hereby incorporated herein by reference.

Catheter 10 of the present invention may be used to deliver a therapeutic agent to any target site in the body. Non-limiting examples of such target sites include any body lumina and organ such as the coronary vasculature, esophagus, trachea, colon, biliary tract, urinary tract, prostate, brain, lung, liver, heart, skeletal muscle, kidney, bladder, intestines, stomach, pancreas, ovary, cartilage, eye, bone, and the like.

Catheter 10 of the present invention can be used, for example, in any application for treating, preventing, or otherwise affecting the course of a disease or tissue or organ dysfunction. For example, catheter 10 and the method of delivering a therapeutic agent to a target site using catheter 10 of the present invention can be used to induce or inhibit angiogenesis, as desired, to present or treat restenosis, to treat a cardiomyopathy or other dysfunction of the heart, for treating Parkinson's disease or a stroke or other dysfunction of the brain, for treating cystic fibrosis or other dysfunction of the lung, for treating or inhibiting malignant cell proliferation, for treating any malignancy, and for inducing nerve, blood vessel or tissue regeneration in a particular tissue or organ.

The foregoing description has been set forth merely to illustrate the invention and is not intended as being limiting. Each of the disclosed embodiments may be considered individually or in combination with other embodiments of the invention, other variations, and other aspects of the invention. Modifications of the disclosed embodiments incorporating the spirit and substance of the invention may occur to persons skilled in the art and such modifications are within the scope of the present invention.

We claim:

1. A catheter comprising:
    a hollow, flexible tube having an infusion lumen extending partially therethrough and
    a drug delivery unit within a distal end of the tube and adapted to be adjacent to a target site in the body, the drug delivery unit comprising:
        an actuator in fluid communication with the infusion lumen of the tube, the actuator having an un-expanded inactivated configuration and an expanded activated configuration;
        a receptacle in communication with the actuator such that the actuator transmits force to the receptacle in the activated configuration, and
        a retractable needle in fluid communication with a distal end of the receptacle.

2. The catheter of claim 1, wherein the receptacle is a drug delivery balloon.

3. The catheter of claim 1, wherein the drug delivery unit further comprises a drug delivery lumen extending partially therethrough, the drug delivery lumen in fluid communication with the receptacle at one end and in fluid communication with the needle at another end.

4. The catheter of claim 3, wherein a pressure-sensitive membrane is located between the receptacle and the drug delivery lumen.

5. The catheter of claim 1, wherein the actuator is a balloon.

6. The catheter of claim 1, wherein the actuator is a piston.

7. The catheter of claim 6, wherein the piston has an O-ring disposed therearound, the O-ring contacting opposing inner side surfaces of the catheter.

8. The catheter of claim 6, wherein the piston is slidably received within the catheter with a close tolerance fit between an outer surface of the piston and opposing inner side surfaces of the catheter.

9. The catheter of claim 1, wherein the actuator is a spring-loaded coil.

10. The catheter of claim 1, wherein the actuator is fabricated of a temperature-sensitive material having a transition temperature, the actuator assuming an activated configuration when the temperature-sensitive material reaches the transition temperature.

11. The catheter of claim 1, wherein the receptacle is a balloon.

12. The catheter of claim 1, wherein the receptacle is a chamber.

13. The catheter of claim 12, wherein the chamber has a front end defined by a first pressure-sensitive gate.

14. The catheter of claim 13, wherein the chamber has a back end defined by a second pressure sensitive gate.

15. The catheter of claim 12, wherein the chamber has a back end defined by a pressure sensitive gate.

16. The catheter of claim 1, wherein the actuator is a first balloon and the receptacle is a second balloon.

17. The catheter of claim 1, wherein the actuator comprises a first primary balloon and a first secondary balloon and the receptacle comprises a second balloon, the second balloon disposed between the first primary balloon and the first secondary balloon.

18. The catheter of claim 1, wherein the actuator is a plurality of balloons.

19. The catheter of claim 1, further comprising a plurality of drug delivery units.

20. The catheter of claim 19, wherein each of the drug delivery units holds a different therapeutic agent.

21. A catheter comprising:
a hollow, flexible tube comprising an inner shaft having an infusion lumen extending partially therethrough, an outer shaft disposed around the inner shaft, and a drug delivery unit within a distal end of the tube and adapted to be adjacent to a target site in the body, the drug delivery unit comprising:
an actuator in fluid communication with the infusion lumen, the actuator having an unexpanded inactivated configuration and an expanded activated configuration; and
a receptacle in fluid communication with a retractable needle, the receptacle and actuator in communication with each other, such that the actuator transmits force to the receptacle in the activated configuration.

22. A method of delivering a therapeutic agent to a target site comprising:
providing a catheter having a distal end comprising a drug delivery unit;
placing a therapeutic agent in the drug delivery unit; and
delivering the therapeutic agent to the target site.

23. The method of claim 22, wherein the catheter comprises a needle at the distal end thereof.

24. The method of claim 23, wherein placing a therapeutic agent in the drug delivery unit comprises accessing the drug delivery unit through the needle of the catheter.

25. The catheter of claim 1, further comprising a therapeutic agent within the receptacle.

26. A catheter comprising:
a flexible, hollow tube having a proximal end adapted to receive an infusion material, a distal end adapted to deliver a therapeutic to a patient, and an infusion lumen extending partially therethrough, the tube comprising:
a drug delivery unit at the distal end of the tube, the drug delivery unit comprising:
an actuator at a distal end of the infusion lumen and in fluid communication therewith, the actuator having an inactivated configuration and an activated configuration;
a therapeutic receptacle distal to the actuator,
a retractable needle at a distal end of the therapeutic receptacle,
wherein the actuator transmits force to the therapeutic receptacle in the activated configuration to deliver a therapeutic to the patient.

27. The catheter of claim 26, wherein when in use, infusion material travels through the infusion lumen to place the actuator in the activated configuration.

28. The catheter of claim 26, wherein when in use, force transmitted to the therapeutic receptacle delivers a therapeutic through the needle to a target site.

29. The catheter of claim 26, wherein an interior of the receptacle is fluidly isolated from the infusion lumen and the actuator.

* * * * *